United States Patent [19]

Fogel

[11] Patent Number: 5,476,643
[45] Date of Patent: Dec. 19, 1995

[54] METHOD OF DISPERSING MICRONIZED $TIO_2$, ZNO AND OTHER PIGMENTS

[75] Inventor: Arnold W. Fogel, Upper Saddle River, N.J.

[73] Assignee: Bernel Chemical Co., Englewood, N.J.

[21] Appl. No.: 154,785

[22] Filed: Nov. 19, 1993

[51] Int. Cl.$^6$ .............................. A61K 7/42; A61K 7/50; C01G 28/00
[52] U.S. Cl. .................... 423/610; 424/59; 514/846; 554/213; 554/175
[58] Field of Search .................. 423/610; 260/410.6

[56] References Cited

U.S. PATENT DOCUMENTS 3,651,102  3/1972  Coopersmith ..................... 260/410.6
4,940,577  7/1990  Greenberg et al. .................. 424/59
5,116,604  5/1992  Fogel et al. ........................ 424/59

*Primary Examiner*—Dale R. Ore
*Attorney, Agent, or Firm*—Anthony D. Cipollone

[57] ABSTRACT

A novel use of two specific neopentyl glycol diesters as wetting, dispersing, spreading and deterging agents for micronized $TiO_2$, ZnO and other pigments is introduced. These esters, neopentyl glycol di-2-ethyl hexanoate and neopentyl glycol di-isostearate, are used in varying combinations and may also be used with an emulsifying agent for a water dispersible pigmented make-up cleaner composition.

6 Claims, No Drawings

METHOD OF DISPERSING MICRONIZED TIO₂, ZNO AND OTHER PIGMENTS

BACKGROUND OF THE INVENTION

There has been a recent upsurge in searching for a better method of wetting, dispersing, spreading and deterging micronized $TiO_2$, ZnO and other pigments in dermatological cosmetic formulations.

Previously octyldodecyl neopentoanoate, the subject of U.S. Pat. No. 5,116,604, has been introduced and used by this inventor as a method of wetting $TiO_2$.

The present invention introduces the use of a combination of two specific neopentyl glycol diesters as the dispersant for these pigments.

DESCRIPTION OF PRIOR ART

U.S. Patent No. 3,651,102 describes the preparation of glycol diesters.

U.S. Pat. No. 4,648,908 presents coated pigment and cosmetic materials comprising coated pigments.

U.S. Pat. No. 4,749,563 teaches skin treatment compositions such as sunscreen and moisturizer compositions including a secondary amide to impart moisture resistance or substantivity to the compositions.

U.S. Pat. No. 4,847,069 introduces photoprotection compositions comprising sorbohydroxanic acid and an anti-inflammatory agent.

U.S. Pat. No. 4,933,177 has as its object cosmetic compositions for treatment of hair and skin containing powder particles resulting from the pulverization of at least one plant substance and a cohesion agent.

U.S. Pat. No. 4,946,671 deals with the same type as U.S. Pat. No. 4,847,069.

U.S. Pat. No. 5,238,965 relates to methods for regulating wrinkles in mammalian skin.

OBJECT OF THE INVENTION

It is the object of this invention to introduce a novel use of two specific neopentyl glycol diesters as wetting, dispersing, spreading and deterging agents for micronized ZnO, $TiO_2$, and other pigments.

SUMMARY AND DESCRIPTION OF THE INVENTION

Neopentyl glycol reacts with isostearic acid and 2-ethyl hexanoic acid to produce the neopentyl glycol diesters as follows:

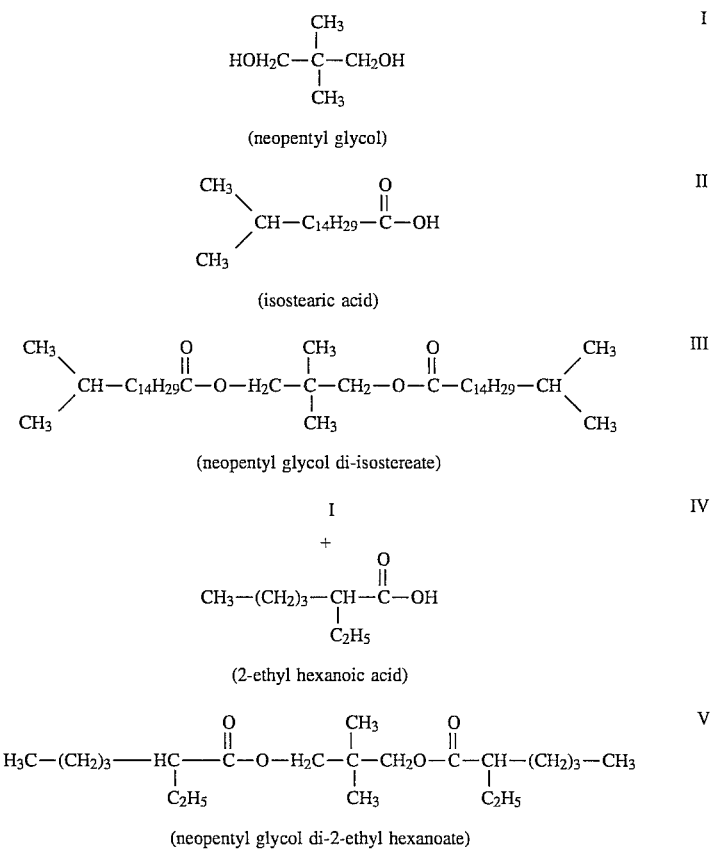

Another unique advantage introduced by the present invention is the ease with which the pigment is incorporated into the ester. It eliminates the need for special mixing and grinding equipment. Simple stirring with ordinary lab propeller mixers will produce the desired results.

Following are examples of the use of the instant invention. In the first four (4) examples the neopentyl glycol diesters wet the pigment almost instantly. This will be immediately obvious to those skilled in the art and practicing the art.

Example 1

| | |
|---|---|
| Neopentyl glycol di-2-ethyl hexanoate | 18.0 parts (66.⅔%) |
| Neopentyl glycol di-isostearate | 2.0 parts |
| Micronized TiO₂ | 10.0 parts (33.⅓% w/w TiO₂) |

Stir until uniform.

Example 2

| | |
|---|---|
| Neopentyl glycol di-2-ethyl hexanoate | 27.0 parts (75.0%) |
| Neopentyl glycol di-isostearate | 3.0 parts |
| Micronized ZnO | 10.0 parts (25.0% w/w ZnO) |

Stir until uniform.

Example 3

| | |
|---|---|
| Neopentyl glycol di-isostearate | 27.0 parts (75.0%) |
| Neopentyl glycol di-2-ethyl hexanoate | 3.0 parts |
| Micronized ZnO | 10.0 parts (25.0% w/w ZnO) |

Stir until uniform.

Example 4

| | |
|---|---|
| Neopentyl glycol di-isostearate | 18.0 parts (66.⅔%) |
| Neopentyl glycol di-2-ethyl hexanoate | 2.0 parts |
| Micronized TiO₂ | 10.0 parts (33.⅓% w/w TiO₂) |

Stir until uniform.

EXAMPLE 5

Pigmented Suntan Lotion

PHASE A 15° C. – 25° C. (room Temp.); Mix until "smooth":

| | |
|---|---|
| Hetester ® PHA | 10.00 |
| Minno ™ 21 | 10.00 |
| TiO₂ Micronized | 10.00 |

PHASE B (room temp.):

| | |
|---|---|
| Water, deionized | 68.90 |

PHASE C (Dry Blend):

| | |
|---|---|
| Veegum ® | 0.70 |
| Keltrol ® | 0.30 |

PHASE D:

| | |
|---|---|
| Kathon ® CG | 0.10 |
| | 100.00% TOTAL |

PROCEDURE: Add Phase C to Phase B and mix until "smooth". Then, with proper mixing (propeller causing a vortex), add Phase A. Mix until uniform and add Phase D. Mix until uniform.

In the above five examples, the Minno™ emollient wets the pigment almost instantly. This will be immediately obvious to those practicing the art.

EXAMPLE 6

Suntan Lotion

PHASE A 40° C.; Mix until dispersed.

| | |
|---|---|
| Hetester ® PHA | 10.00 |
| CUPL ® PIC[1] | 2.00 |
| Minno ™ 21 | 20.00 |
| TiO[2] (Micronized) | 9.00 |
| ZnO (Micronized) | 3.00 |

PHASE B (40° C.)

| | |
|---|---|
| Water, deionized | 54.90 |

PHASE C (Dry Blend)

| | |
|---|---|
| Veegum ® | 0.70 |
| Keltrol ® | 0.30 |

PHASE D

| | |
|---|---|
| Kathon ® CG | 0.10 |
| | 100.00% TOTAL |

PROCEDURE:
Add Phase C to Phase B and mix until "smooth". Then, with proper mixing (propeller causing a vortex), add Phase A. Mix until uniform and add Phase D. Mix until uniform.

EXAMPLE 7

Water Dispersible Pigmented Make-Up Cleaner

| | |
|---|---|
| Minno ™ 21 | 40.00 |
| Minno ™ 41 | 40.00 |
| Hetester PHA | 20.00 |
| | 100.00% TOTAL |

Example 7 is a water dispersible make-up cleaner. This formulation will wet, disperse and clean the pigmented product off the skin. The Hetester® PHA makes the dispersion of Minno™ and pigment removable by water.

| | |
|---|---|
| Hetester ® PHA | Propylene glycol isoceteth-3-acetate |
| Veegum | Magnesium aluminum silicate |
| Keltrol | Xanthan gum |
| Kathon CG | Methylchloroisothiazolinone (and) methylisothiazolinone |
| Cupl ® PIC | Dipropylene glycol isoceteth-20 acetate |
| Minno ™ 41 | 90%/10% weight/weight ratio |
| | neopentyl glycol di-isostearate |
| | neopentyl di-2-ethyl hexanoate |
| Minno ™ 21 | 90%/10% weight/weight ratio |
| | neopentyl di-2-ethyl hexanoate |
| | neopentyl glycol di-isostearate |

What is claimed is:

1. A method of wetting, dispersing, spreading and deterging micronized pigments comprising: neopentyl glycol di-isostearate and neopentyl glycol di-2-ethyl hexanoate as the esters which are the wetting, dispersing, spreading and deterging compounds; said esters varying in weight/weight ratio from 90.% neopentyl glycol di-isostearate, 10% neopentyl di-2-ethyl hexanoate to 10% neopentyl d-2-ethyl hexanoate/90% neopentyl glycol di-isostearate and a micronized pigment selected from a group consisting of ZnO and $TiO_2$.

2. The method of claim 1 wherein the said esters varying in range 80%–60% by weight combined with 20%–40% of said micronized pigment.

3. The method of claim 1 wherein the pigment is ZnO.

4. The method in claim 1 wherein the pigment is $TiO_2$.

5. The method of claim 1 wherein said esters comprise 75.0% by weight and the micronized pigment is ZnO comprising 25.0% by weight.

6. The method of claim 1 wherein said esters comprise 66⅔% by weight and the micronized pigment is $TiO_2$ comprising 33⅓% by weight.

* * * * *